United States Patent

Dafinger et al.

Patent Number: 5,233,106
Date of Patent: Aug. 3, 1993

[54] PROCESS FOR THE HYDROGENATION OF CHLOROMETHANES

[75] Inventors: Willi Dafinger, Emmerting; Ludwig Schmidhammer, Haiming, both of Fed. Rep. of Germany

[73] Assignee: Wacker-Chemie GmbH, Munich, Fed. Rep. of Germany

[21] Appl. No.: 910,215

[22] Filed: Jul. 9, 1992

[30] Foreign Application Priority Data

Jul. 15, 1991 [DE] Fed. Rep. of Germany ....... 4123396

[51] Int. Cl.$^5$ .................. C07C 17/24; C07C 19/02
[52] U.S. Cl. .................................................. 570/176
[58] Field of Search ......................................... 570/176

[56] References Cited

U.S. PATENT DOCUMENTS 2,992,280  7/1961  Olstawski et al. ................ 570/176
3,579,596  5/1971  Mullin et al. ..................... 570/176

FOREIGN PATENT DOCUMENTS 0432636  6/1991  European Pat. Off.

Primary Examiner—Werren B. Lone
Attorney, Agent, or Firm—Burgess, Ryan & Wayne

[57] ABSTRACT

A process is provided for the hydrogenation of chloromethanes of the formula $CH_nCl_m$, where $n=0$ to 3 and $m=4-n$, with hydrogen at a temperature of 150° to 250° C. and under an absolute pressure of 1 to 10 bar, by means of a supported catalyst comprising an activated charcoal support with a BET surface area of more than 500 m$^2$/g, 0.5 to 20% by weight of copper in elemental or chemically bonded form and 0.01 to 1.0% by weight of rhodium or palladium in elemental or chemically bonded form, and with 0.1 to 10.0% by weight of a water-soluble phosphonium halide.

10 Claims, No Drawings

PROCESS FOR THE HYDROGENATION OF CHLOROMETHANES

BACKGROUND OF THE INVENTION

1) Field of the Invention

The invention relates to a process for the hydrogenation of chloromethanes of the formula $CH_nCl_m$, where $n=0$ to 3 and $m=4-n$.

2) Description of the Related Art

In industrial processes for the manufacture of chlorofluoromethanes, the corresponding chloromethanes are predominantly used as educts, in which chlorine is then replaced with fluorine in stages using HF. $CCl_4$, in particular, has hitherto been used as the starting compound for the manufacture of chlorofluorohydrocarbons (CFCs). Thus, starting from $CCl_4$, the series of compounds $CFCl_3$, $CF_2Cl_2$ and $CF_3Cl$ are obtained with increasingly stringent reaction conditions as regards the amount of HF used, the temperature, the pressure and the type and amount of catalyst.

The $CCl_4$ used for the manufacture of CFCs originated predominantly, either as the main product or as a by-product, from the common synthetic processes for the manufacture of chloromethanes. These are the thermal chlorination or catalytic oxychlorination of methane, in which all 4 chloromethane derivatives are obtained together, the chlorolysis process (chlorinating scission of propene or chlorine-containing $C_1$ to $C_3$ residues) and the esterification of methanol with hydrochloric acid to give methyl chloride, followed by further chlorination of the methyl chloride to give more highly chlorinated chloromethanes.

In the strongly exothermic gas phase chlorination of methane (400°-450° C., slight positive pressure), which proceeds via free radicals, all the chlorinated methanes are produced together when the $CH_4/Cl_2$ ratio is equimolar:

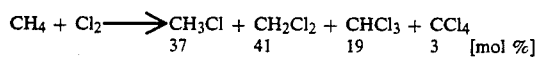

Specific higher chlorination can be achieved by recycling the less highly chlorinated products.

The chlorinating scission of propene at temperatures of 600° to 700° C. and a pressure of 2 to 5 bar produces both perchloroethylene and carbon tetrachloride:

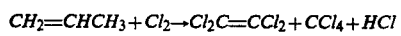

Depending on the reaction conditions and the educt ratio, the quantity ratio $CCl_4$/Per can vary between 65/35 and 35/65, i.e. appreciable amounts of carbon tetrachloride are obtained in all cases.

As the principal use sector for $CCl_4$, namely as an educt in the manufacture of chlorofluorohydrocarbons, will decline in the future because of the massive restrictions on production and the anticipated cessation of production, it was necessary to discover new possible uses for the $CCl_4$ obtained in the afore-mentioned processes.

One possibility is to use $CCl_4$ as an educt for the manufacture of chloromethanes, for example chloroform. Of the chloromethanes, chloroform in particular is currently important as an educt for the manufacture of polytetrafluoroethylene. In the synthesis of the tetrafluoroethylene monomer starting from chloroform, two chlorines are replaced with fluorine in the first step:

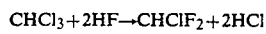

The subsequent thermal dehydrochlorination of $CHClF_2$ produces monomeric tetrafluoroethylene:

The object was therefore to develop a process for the manufacture of chloromethanes, especially chloroform, which starts from more highly chlorinated chloromethanes, for instance carbon tetrachloride, as the educt.

SUMMARY OF THE INVENTION

The object was achieved by a hydrogenation process which uses a supported catalyst containing copper (elemental or chemically bonded), a rhodium/palladium compound and a phosphorus compound as active components.

The catalyst according to the invention is known from German patent document A-3941037 as a catalyst for the hydrogenation of perchloroethylene to trichloroethylene. Against this technological background, this catalyst could not be expected to be active in the hydrogenation of chloromethanes as well, since a different reaction mechanism is involved here and the bonding forces of $C_1$ moieties cannot be compared with those of $C_2$ moieties.

The invention relates to a process for the hydrogenation of chloromethanes of the formula $CH_nCl_m$, where $n=0$ to 3 and $m=4-n$, with hydrogen at a temperature of 150° to 250° C. and under a pressure of 1 to 10 bar, by means of a supported catalyst comprising an activated charcoal support with a BET surface area of more than $500 m^2/g$, 0.5 to 20% by weight of copper in elemental or chemically bonded form and 0.01 to 1.0% by weight of rhodium or palladium in elemental or chemically bonded form, and with 0.1 to 10.0% by weight of a water-soluble phosphonium halide.

DESCRIPTION OF THE PREFERRED EMBODIMENTS

The process according to the invention is preferably suitable for the hydrogenation of methylene chloride, chloroform and carbon tetrachloride to the correspondingly less highly chlorinated compounds. It is particularly suitable for the manufacture of chloroform from carbon tetrachloride.

The catalyst support used is activated charcoal, preferably in granular form. In a preferred embodiment, the grain size is 2 to 10 mm. The activated charcoal support has a BET surface area of more than $500 m^2/g$, preferably of 500 to $1400 m^2/g$.

The copper is applied to the support, in elemental or chemically bonded form, in an amount of 0.5 to 20.0% by weight, preferably of 5.0 to 15.0% by weight, based on the total weight of the catalyst support and active components. It is particularly preferable to use water-soluble copper salts, especially $CuCl_2$.

Rhodium is used, in elemental or chemically bonded form, in an amount of 0.01 to 1.0% by weight, preferably of 0.02 to 0.2% by weight, based on the total weight of the catalyst support and active components. Water-soluble rhodium compounds, especially complex salts of rhodium (III) chloride, are particularly preferred. Instead of rhodium it is also possible to use palladium in elemental or chemically bonded form and in the same amounts as those indicated for rhodium. Water-soluble palladium compounds, for instance $PdCl_2$, are again particularly preferred here.

In addition, the catalyst support is also impregnated with 0.1 to 10.0% by weight, preferably 3.0 to 7.0% by weight, based on the total weight of the catalyst support and active components, of a water-soluble phosphonium halide. It is preferable to use water-soluble phosphonium halides of the general formula $(Ph_3PR)X$, Ph being a phenyl radical.

R is hydrogen or a substituted or unsubstituted alkyl or aryl radical, examples being methyl, ethyl, propyl, n-butyl, isobutyl, pentyl, hexyl, heptyl, octyl, nonyl, benzyl, p-chlorobenzyl, p-tert-butyl benzyl, allyl, 2-methallyl, chloromethyl, dichloromethyl, iodomethyl, ethoxycarbonylmethyl or acetonyl radicals.

Chloride, iodide or bromide is preferably used as the halide X.

Preferred phosphonium halides are methyltriphenylphosphonium chloride, methyltriphenylphosphonium bromide, ethyltriphenylphosphonium chloride, ethyltriphenylphosphonium bromide, n-propyltriphenylphosphonium chloride, n-propyltriphenylphosphonium bromide, allyl triphenylphosphonium chloride, allyltriphenylphosphonium bromide, n-butyltriphenylphosphonium chloride and n-butyltriphenylphosphonium bromide.

Methyltriphenylphosphonium chloride, methyltriphenylphosphonium bromide, ethyltriphenylphosphonium chloride and ethyltriphenylphosphonium bromide are particularly preferred.

The preparation of the phosphonium halides can be carried out in a manner known per se and is described for example in German patent document A-3941037.

For impregnation, the individual components, namely the copper (salt), the rhodium (salt) or palladium (salt) and the phosphonium compound, preferably in aqueous solution, are applied to the activated charcoal separately or in a mixture, for example by steeping. The catalyst support impregnated in this way is then dried.

To convert chloromethanes, the catalyst is introduced into a reaction tube in bulk form. The reaction is carried out at a temperature of 150° to 250° C. and under an absolute pressure of 1 to 10 bar. The chloromethane compound is preferably reacted in amounts of 0.5 to 5.0 mol per hour and per liter of catalyst volume, together with the 0.1-fold to 2-fold molar amount per hour of hydrogen.

The following Examples serve to illustrate the invention further:

EXAMPLE 1

Granular activated charcoal with a BET surface area of 800 $m^2/g$ and a grain size of 3 mm (Degusorb WS IV Spezial from Degussa) was steeped with aqueous solutions of $CuCl_2$, $Na_3RhCl_6$ and $[(C_6H_5)_3PCH_3]Cl$ and then dried to give a Cu content of the activated charcoal of 10% by weight, an Rh content of 0.044% by weight and a $[(C_6H_5)_3 PCH_3]Cl$ content of 6.5% by weight. The hydrogenation of carbon tetrachloride was carried out in a one-tub reactor with a catalyst volume of 450 ml. The reactor was charged with 64 q/h (0.4 mol/h) of carbon tetrachloride and 9.1 l/h (0.45 mol/h) of hydrogen. The absolute reaction pressure was 4 bar. At a reaction temperature of 200° C., a product mixture of 46.8% by weight of $CCl_4$, 52.5% by weight of $CHCl_3$, 0.602% by weight of $CH_2Cl_2$ and 0.009% by weight of $C_3Cl$ was obtained.

EXAMPLE 2

The procedure was analogous to Example 1, except that methyltriphenylphosophonium bromide was used as the phosphonium halide. The conversion rate was 45% by weight of $CHCl_3$.

EXAMPLE 3

The catalyst prepared in Example 1 was used. The one-tube reactor was filled with a catalyst volume of 450 ml and charged with 47 g/h (0.4 mol/h) of $CHCl_3$ and 9.1 l/h (0.45 mol/h) of $H_2$. The absolute reaction pressure was 4 bar. At a reaction temperature of 200° C., 83.43% by weight of $CHCl_3$ and 14.7% by weight of $CH_2Cl_2$ were obtained after the reaction, the remainder consisting of $CH_3Cl$ and methane.

What is claimed is:

1. A process for the hydrogenation of chloromethane of the formula $CH_nCl_m$, where n=0 to 3 and m=4-n, to provide a less higher clorinated compound which comprises contacting said chloromethane with hydrogen at a temperature of 150° to 250° C. and under an absolute pressure of 1 to 10 bar, in the presence of a supported catalyst comprising an activated charcoal support with a BET surface area of more than 500 $m^2/g$, 0.5 to 20% by weight of copper in elemental or chemically bonded form and 0.01 to 1.0% by weight of rhodium or palladium in elemental or chemically bonded form, and with 0.1 to 10.0% by weight of a water-soluble phosphonium halide.

2. A process as claimed in claim 1, wherein the activated charcoal used is in granular form with a grain size of 2 to 10 mm and a BET surface area of 500 to 1400 $m^2/g$.

3. A process as claimed in claim 1, wherein 5.0 to 15.0% by weight, based on the total weight of the catalyst support and active components, is a water-soluble copper salt.

4. A process as claimed in claim 3, wherein said copper salt is $CuCl_2$.

5. A process as claimed in claim 1, wherein 0.02 to 0.2% by weight, based on the total weight of the catalyst support and active components, is a water-soluble rhodium compound or a water-soluble palladium compound.

6. A process as claimed in claim 5, wherein said rhodium compound is rhodium (III) chloride and said palladium compound is palladium (II) chloride.

7. A process as claimed in claim 1, wherein a phosphonium compound of the general formula $(Ph_3PR)X$ is used, Ph being a phenyl radical, R being hydrogen or a substituted or unsubstituted alkyl or aryl radical and X being chloride, bromide or iodide.

8. A process as claimed in claim 7, wherein the water-soluble phosphonium halide is selected form the group consisting of methyltriphenyl phosphonium chloride, methyltriphenylphosphonium bromide, ethyltriphenylphosphonium chloride and ethyltriphenylphosphonium bromide.

9. A process as claimed in claim 1, wherein the chloromethane compound is reacted in amounts of 0.5 to 5.0 mol per hour and per liter of catalyst volume, together with the 0.1-fold to 2-fold molar amount per hour of hydrogen.

10. A process as claimed in claim 1 wherein the chloromethane is carbon tetrachloride.

* * * * *